United States Patent [19]

Giori et al.

[11] 4,002,979
[45] Jan. 11, 1977

[54] PULSE COMPARATOR

[75] Inventors: Francis A. Giori, Clarence; Anthony J. DiTusa, Williamsville, both of N.Y.

[73] Assignee: Electro Sciences for Medicine, Inc., Clarence, N.Y.

[22] Filed: Dec. 12, 1974

[21] Appl. No.: 532,257

Related U.S. Application Data

[60] Division of Ser. No. 353,118, April 20, 1973, Pat. No. 3,854,472, which is a continuation-in-part of Ser. No. 84,646, Oct. 28, 1970, abandoned.

[52] U.S. Cl. .............................. 324/181; 324/78 D
[51] Int. Cl.² ......................................... G04F 8/00
[58] Field of Search ............. 324/78 D, 78 N, 78 Z, 324/79 D, 83 D, 181, 83 A, 188, 190; 340/146.2; 235/92; 84/454

[56] References Cited

UNITED STATES PATENTS

| 3,337,796 | 8/1967 | Hentschel | 324/83 A |
|---|---|---|---|
| 3,535,620 | 10/1970 | Johnston | 324/181 |
| 3,559,066 | 1/1971 | Pincus | 324/78 D |
| 3,711,772 | 1/1973 | Brown | 324/78 D |
| 3,735,347 | 5/1973 | Whitney | 324/78 D |
| 3,766,818 | 10/1973 | Prohofsky | 84/454 |

*Primary Examiner*—Palmer C. Demeo
*Assistant Examiner*—Michael J. Tokar
*Attorney, Agent, or Firm*—Christel & Bean

[57] ABSTRACT

Electrical pulse width measuring apparatus wherein the presence of a pulse of unknown time duration is utilized to initiate generation of a reference pulse of known time duration. The reference pulse is generated by means including a monostable multivibrator together with a controlled driving circuit connected to the multivibrator timing capacitor. The time duration of the reference pulse accordingly is made linearly proportional to an input control variable such as a manually adjustable dial setting. The unknown and reference pulses are applied as inputs to a flip-flop circuit, the final state of which is determined by the pulse of longer time duration. An indicator coupled to the flip-flop circuit provides a visual indicator of the final state thereof. The apparatus can be used to measure or monitor a signal occuring in the body of a patient, such as the artifact pulse from an implanted cardiac pacemaker. The apparatus includes means to condition the artifact pulse and to generate a standardized pulse which accurately represents the width of the pacemaker pulse, and the apparatus further includes means for indicating when the width of the pacemaker pulse changes by a predetermined amount.

7 Claims, 3 Drawing Figures

PULSE COMPARATOR

This is a division of application Ser. No. 353,118 filed Apr. 20, 1973, now U.S. Pat. No. 3,854,472, which is a continuation-in-part of application Ser. No. 84,646, filed Oct. 28, 1970, and now abandoned.

BACKGROUND OF THE INVENTION

This invention relates to the art of electrical measurement, and more particularly to novel apparatus for measuring the time duration or width of an electrical pulse.

In many instances it is important, if not essential, to determine the time duration or width of an unknown electrical pulse with a significant degree of accuracy or to adjust the width of a pulse precisely to some desired value. One exemplary area of use of the present invention is in medical electronics, where pulses indicative of physiological activity are to be inspected and measured, or where pulses employed to stimulate or influence physiological activity are to be controlled accurately.

A practical and economical approach to pulse measurement would be to compare the time duration of an unknonw electrical pulse to the time duration of a precise, calibrated reference pulse. This approach should have a capability for handling pulses of considerably different amplitudes and shapes as well as pulses of durations occurring in a considerably wide range.

SUMMARY OF THE INVENTION

It is, therefore, an object of this invention to provide a new and improved pulse width measuring apparatus for comparing the time duration of an unknown pulse with the time duration of a known, reference pulse.

It is an additional object of this invention to provide such apparatus operable with unknown pulses having time durations in a relatively wide range.

It is a further object of this invention to provide such apparatus which is operable with unknown pulses having considerably different waveshapes and amplitudes.

It is a further object to provide such apparatus capable of generating a reference pulse having a width or time duration linearly proportional to a control input or dial setting.

It is a further object of this invention to provide such apparatus capable of measuring or monitoring pulse signals occuring in the body of a patient.

The present invention provides electrical pulse width measuring apparatus wherein the presence of a pulse of unknown time duration is utilized to initiate generation of a reference pulse of known time duration. The reference pulse is generated in a manner whereby the time duration is linearly proportional to an input control variable, such as a manually adjustable dial setting. The unknown and reference pulses are applied as inputs to a two state circuit, the final state of which is determined by the pulse of longer time duration. An indication is provided as to whether the unknown pulse is of shorter, the same or longer time duration as compared to the reference pulse.

The foregoing and additional advantages and characterizing features of the present invention will become clearly apparent upon a reading of the ensuing detailed description together with the included drawing wherein:

BRIEF DESCRIPTION OF THE DRAWING FIGURES

DETAILED DESCRIPTION OF THE ILLUSTRATED EMBODIMENT

Figure 1:
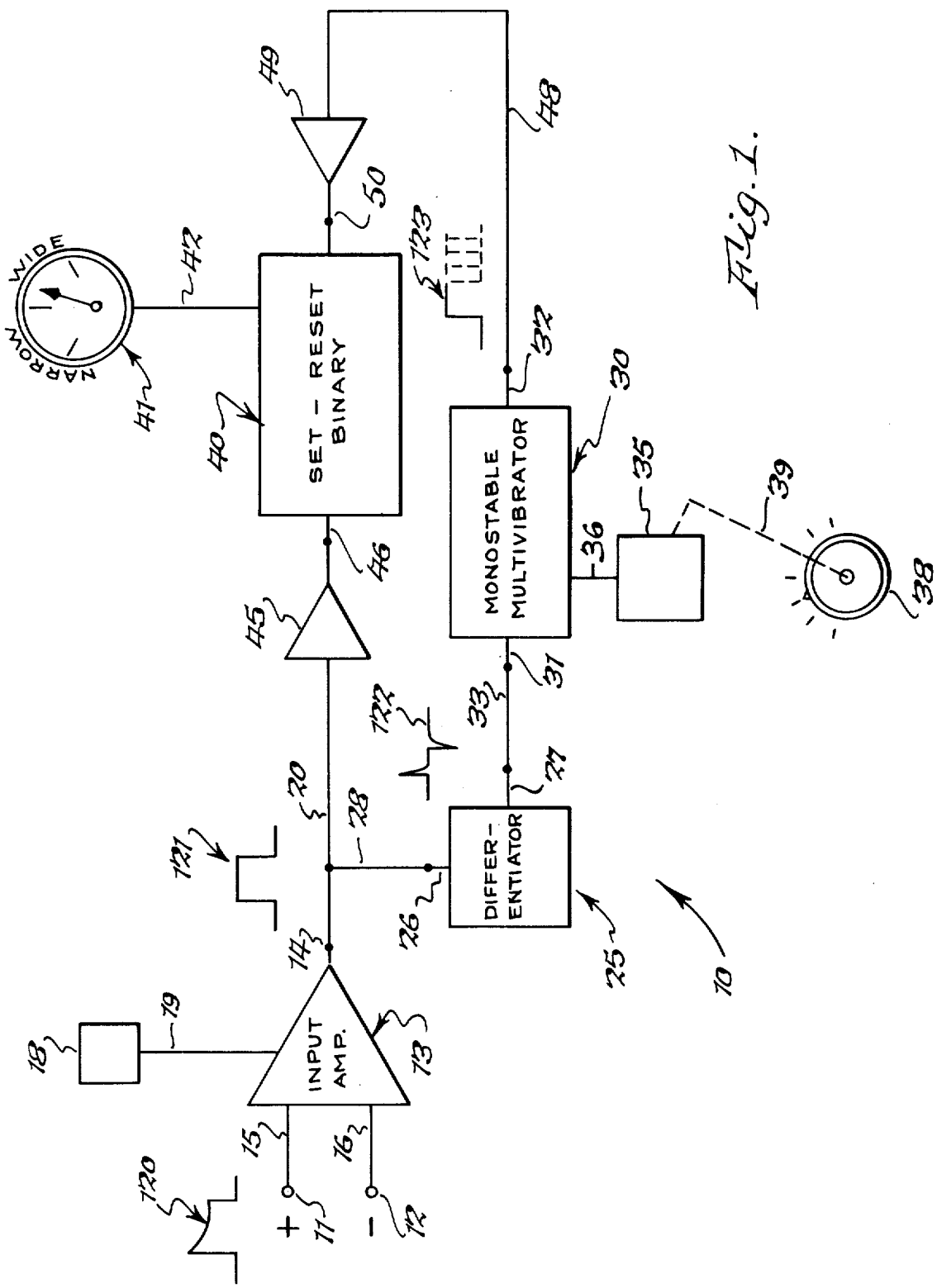
FIG. 1 is a block diagram of electrical pulse width measuring apparatus according to the present invention.

FIG. 1 shows in block diagram form a pulse width measuring apparatus, generally designated 10, according to the present invention. The apparatus 10 of FIG. 1 includes a pair of input terminals 11 and 12 to which is applied an unknown pulse, the time duration or width of which is to be measured. A pulse, of course, represents the amplitude of voltage or current over a period of time. The apparatus 10 further includes an amplifier 13 having an output 14, and leads 15, 16 connect the apparatus input terminals 11, 12, respectively, to corresponding input terminals of amplifier 13. A threshold adjusting means 18 is connected through a lead 19 to amplifier 13 for controlling the region on the unknown pulse at which the duration is measured. An amplified version of the input, unknown pulse thus is available on line 20 which is connected to amplifier output 14. The apparatus 10 of the present invention utilizes the presence of the unknown pulse to initiate generation of a reference pulse of known width or time duration. In particular, apparatus 10 further comprises synchronizing means in the form of a differentiator circuit 25 having an input 26 and an output 27. A lead 28 connects line 20 to input 26 of circuit 25 whereby the amplified pulse is differentiated to provide a relatively sharp trigger pulse available on output 27.

The pulse width measuring apparatus 10 further includes reference pulse producing means, indicated generally at 30, having an input 31 and an output 32. Pulse producing means 30 preferably comprises a monostable multivibrator, the construction and operation of which will be described in more detail presently. A line 33 connects differentiator output 27 with pulse producing means input 31 whereby trigger pulses are applied to the multivibrator in means 30 for initiating operation of the same. According to the present invention a driving circuit 35 is connected through a line 36 to the multivibrator of means 30. A manually-adjusted or operated control dial 38 also is included and is operatively connected to driving circuit 35 as indicated by the broken line 39. Dial 38 has associated therewith indicia for selecting a reference pulse width as determined by a suitable calibration. According to the present invention, the time duration or width of the reference pulse appearing on output terminal 32 of means 30 is linearly proportional to the setting or selected position of dial 38. In other words, the reference pulse of known duration is generated by means 30 in a manner whereby the duration is linearly proportional to an input control variable, such as the manually adjustable setting of dial 38.

The two electrical pulses of known and unknown duration are applied as inputs to a comparison means which in the present instance comprises a two state circuit 40, the particular state of which is determined by the input pulse of longer duration. An indicator represented schematically at 41 is connected through a line 42 to circuit 40 and provides an indication as to whether the unknown pulse is shorter or longer in width or time duration as compared to the reference pulse. In particular, line 20, on which the unknown pulse is present, is connected through a buffer amplifier 45 to one input terminal 46 of circuit 40. Output terminal 32 of means 30, on which the reference pulse is present, is connected by a line 48 and through a buffer amplifier 49 to a second input terminal 50 of circuit 40. By way of illustration, the position of the arrow of indicator 41 as shown in FIG. 1 would indicate that the unknown pulse is relatively wide as compared to the reference pulse. A movement of the arrow to the left-hand region of the dial face of indicator 41 in the present illustration, on the other hand, would indicate that the unknown pulse is relatively narrow as compared to the reference pulse. A preferred form of indicator 41 and its relation to circuit 40 will be described in more detail presently.

Figure 2:
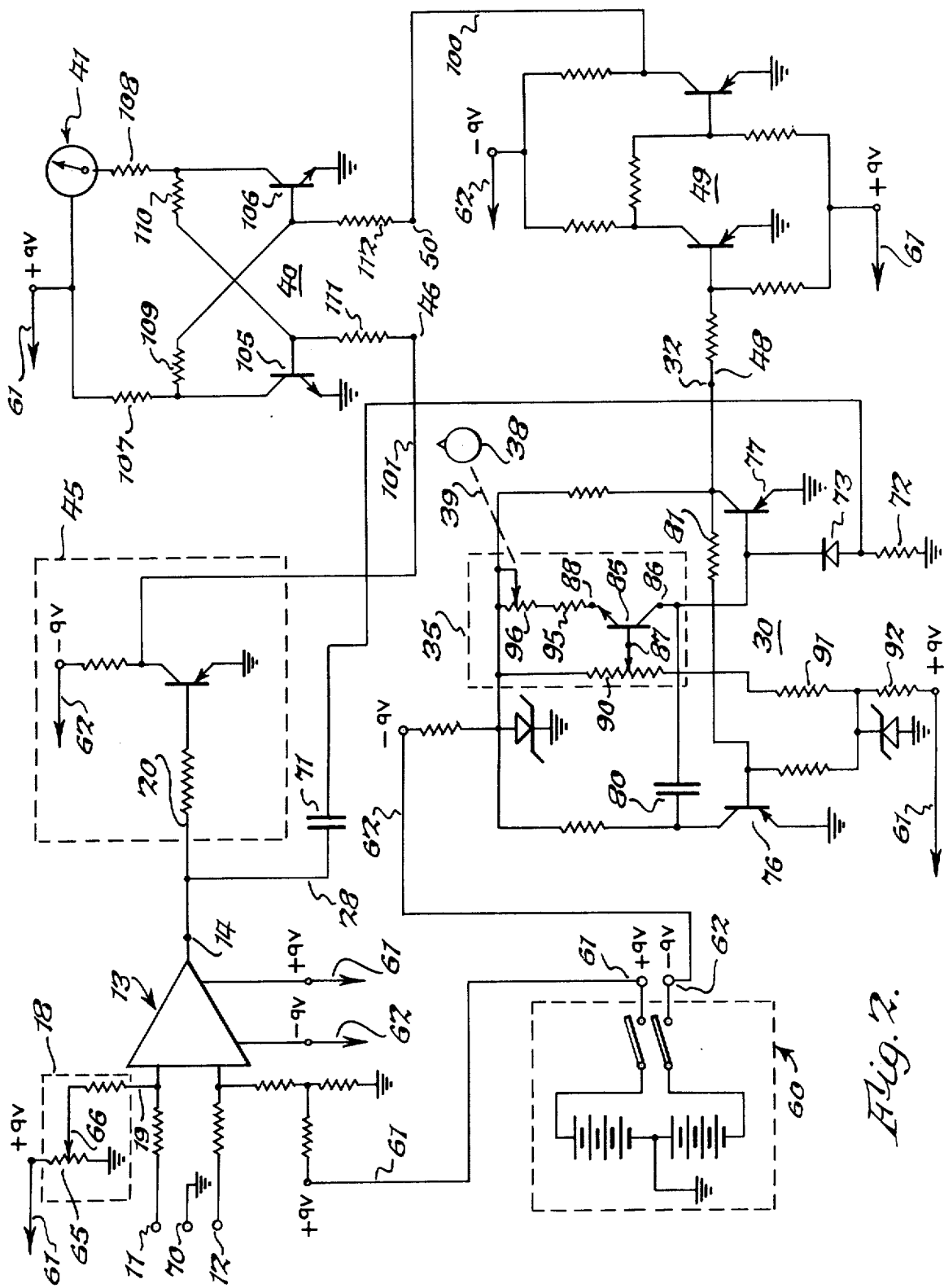
FIG. 2 is a schematic diagram of a presently preferred circuit for the apparatus of FIG. 1.

FIG. 2 shows a preferred electrical circuit for the apparatus 10 of FIG. 1. A power supply 60 includes two batteries connected at appropriate terminals to a ground or reference point and of a magnitude whereby a bias voltage of about 9 volts positive is available on terminal 61 and a bias voltage of about 9 volts negative is available on a terminal 62. These terminals, in turn, are connected by leads (not all shown) to various points of the circuit as will be apparent hereafter. Amplifier 13 should be of a variety which is free from overload difficulties, to be compatible with widely variable levels and waveshapes of the input signals. One type of amplifier 13 found to be particularly suitable is the type designated MC 1439 which has the capability of amplifying input pulses over a wide range of pulse heights, for example from about 1.0 millivolts to about 500 millivolts. According to the present invention, amplifier 13 is provided with a threshold control 18 comprising a potentiometer 65, one terminal of which is connected through a lead to the positive bias voltage terminal 61, the other terminal of potentiometer 65 being connected to ground. The wiper arm 66 of potentiometer 65 is connected through a resistor and lead 19 to one input of amplifier 13. The adjustment of the threshold of amplifier 13 provided by the adjustment of potentiometer 65 enables control of the amplifier switching point, i.e. pulse slicing levels. With this adjustment the region on the pulse at which the duration is measured or sampled can be controlled, which amounts to passing a portion of the input waveform as measured in the amplitude direction. As a result, pulses of widely different amplitudes and having other than rectangular waveforms can be examined. In addition, this alleviates the problem of a false indication of a wide pulse resulting from saturation of amplifier 13 in response to a direct voltage level being present in addition to the pulse being examined.

The pulse of unknown width or time duration is applied to input terminals 11, 12 which are referenced to a terminal 70 connected to ground. The substantially rectangular and amplified pulse appearing at the output of amplifier 14 is differentiated by differentiator 25 which includes a capacitor 71, one termimal of which is connected through a lead 28 to line 20 and amplifier output 14. The positive-going and negative-going pulses corresponding to the leading edge and trailing edge, respectively, of the unknown pulse appear across a resistor 72 connected between the other terminal of capacitor 71 and ground. A diode 73 is connected to resistor 72 and poled in a manner such that only the positive-going trigger pulses are applied to the input of reference pulse producing means 30.

Reference pulse producing means 30 includes first and second switching transistors 76 and 77, respectively, connected so as to operate as a monostable multivibrator. The construction and operation of a transistor multivibrator of the monostable variety are readily understood by those skilled in the art so that a detailed description thereof is deemed to be unnecessary. Suffice it to say that transistors 76 and 77 in the present illustration each are of the PNP variety, the emitter terminals of each of which are connected to ground. A negative bias voltage from terminal 62 is connected by a lead through a resistor divider network to each of the collector terminals of transistors 76 and 77. The collector terminal of transistor 76 is coupled through an energy storage means in the form of capacitor 80 to the base terminal of transistor 77, and the collector terminal of transistor 77 is connected through a resistor 81 to the base terminal of transistor 76. The stable condition or state of the multivibrator is with transistor 76 off or non-conducting and transistor 77 on or conducting. Capacitor 80 comprises the timing capacitor for the multivibrator and the magnitude of the capacitance determines the width or time duration of the output pulse generated by means 30.

Driving circuit 35 according to the present invention comprises a transistor 85 having collector, base and emitter terminals 86–88, respectively. Collector terminal 86 is connected to capacitor 80 and to the base terminal of transistor 77. Base terminal 87 is connected to the wiper arm of a potentiometer 90. One terminal of potentiometer 90 is connected through resistors 91 and 92 to a lead connected to positive bias voltage terminal 61, and the other terminal of potentiometer 90 is connected to the voltage divider network connecting the collectors of transistors 76, 77 to the negative bias voltage terminal 62. The emitter terminal 88 is connected through the series combination of fixed resistor 95 and variable resistor 96 to the terminal of potentiometer 90 which is connected in the negative bias voltage supply network.

The reference pulse produced by means 30 is available on terminal 32 and applied through lead 48 to the input of amplifier 49. Amplifier 49 is a two stage transistor amplifier, and the transistors therein are biased such that if one stage is in saturated condition the other stage is in cutoff condition. The output of amplifier 49 is connected through a lead 100 to input terminal 50 of circuit 40. Likewise, the unknown pulse to be measured is applied through lead 20 to the input of a single stage transistor amplifier 45, the output of which is connected through a lead 101 to input terminal 46 of circuit 40. The transistor of amplifier similarly is biased as to normally be in saturation. As a result, the reference and unknown pulses are buffered by the saturated amplifiers 49 and 45, respectively, to equalize the drive potentials.

Circuit 40 in preferred form is similar to a transistor flip-flop of the set-reset variety. In particular, circuit 40 includes first and second switching transistors 105 and 106, respectively, both of the NPN variety and connected together in a bistable multivibrator configuration. The emitter terminals of transistors 105, 106 each are connected to ground. The collector terminal of transistor 105 is connected through a resistor 107 to a lead connected to positive bias voltage terminal 61. The collector terminal of transistor 106 is connected through the series combination of a resistor 108 and indicator 41 to the same lead connected to positive bias voltage terminal 61. Indicator 41 preferably comprises a meter responsive to an electrical quantity, for example an ammeter. In addition, meter 41 is set to read either full scale or zero deflection corresponding to the presence or absence, respectively, of a flow of current through resistor 108 which, in turn, is determined by the state of transistor 106. The collector terminal of transistor 105 is connected through a resistor 109 to the base terminal of transistor 106, and similarly the collector terminal of transistor 106 is connected through a resistor 110 to the base terminal of transistor 105. The base terminal of transistor 105 is connected through a resistor 111 to input terminal 46, and the base terminal of transistor 106 is connected through a resistor 112 to circuit input terminal 50.

The apparatus of the present invention operates in the following manner. An input pulse of unknown width or time duration is indicated generally at 120 in FIG. 1 and is applied to input terminals 11, 12. The amplified version of the unknown pulse provided by amplifier 13 is available on line 20 and indicated at 121 in FIG. 1. Pulse 121 is applied through line 28 to differentiator 25 whereupon trigger pulses indicated at 122 in FIG. 1 are present on line 33. The positive-going trigger pulses 122 are produced by differentiation of the leading edge of pulse 121 and the negative-going trigger pulses from differentiation of the trailing edge of pulse 121. It will be recalled that the provision of diode 73 in the circuit of FIG. 2 insures that only the positive-going trigger pulses, corresponding in time to the leading edge of pulse 121, are utilized to initiate generation of a reference pulse by generating means 30.

Accordingly, the presence of the appropriate trigger pulse on line 33 causes generating means 30 to provide a reference pulse at the output 32 thereof. Such a reference pulse is designated 123 in FIG. 1, and the broken line portion thereof indicates that reference pulse 123 is of variable time duration or width as determined by the setting of dial 38. Furthermore, the variation in width or time duration of reference pulse 123 is linearly directly proportional to the manual adjustment or setting of dial 38. Referring now to FIG. 2, reference pulse producing means 30 comprises a monostable multivibrator, and in this particular illustration the single stable state thereof is with transistor 76 off or nonconducting and transistor 77 on or conducting. This is apparent from an inspection of the transistor types together with the bias voltage polarity and connections therebetween and assuming the absence of a trigger pulse in resistor 72. A positive-going trigger pulse present in resistor 72, corresponding to the leading edge of an unknown pulse present at the output of amplifier 13, is transmitted by diode 73 to drive the base terminal of transistor 77 positive thereby turning transistor 77 off. The resulting decrease in the collector voltage of transistor 77 in the negative direction is transmitted through resistor 81 to the base terminal of transistor 76 thereby turning transistor 76 on. Current then flows to charge capacitor 80, and when the voltage thereacross reaches a sufficient value, transistor 77 is turned on and transistor 76 turned off according to the normal mode of operation for a multivibrator. Accordingly, the output pulse available on terminal 32, which is the reference pulse for this circuit, has a width or time duration determined by the time required for capacitor 80 to charge to the necessary level.

Capacitor 80 charges at a constant rate equal to $dg/dt = Cdv/dt = i_c$, which current $i_c$ also flows through the collectoremitter circuit of transistor 85 and the series combination of resistors 95 and 96. Transistor 85 closely approximates a constant current source, the magnitude of $i_c$ being determined by the voltate on base 87 and by the resistance in the transistor emitter circuit. For any particular value of voltage on base terminal 87, as determined by the setting of potentiometer 90, the charging current $i_c$ is inversely proportion to the series resistance connected to the emitter of transistor 85. Since the width or time duration of the output pulse 123 appearing on terminal 32 of circuit 30 also is inversely proportional to $i_c$, the width of the reference pulse 123 is linearly and directly proportional to the particular value or magnitude of variable resistor 96. Accordingly, the wiper arm of resistor 96 is mechanically coupled to a dial 38 as indicated by the broken line 39, whereby a dial reading linearly proportional to reference pulse time duration is obtained. Thus for any setting of dial 38, the voltage on the base terminal 87 of transistor 85 determines the amount of charging current. As a result, the reading of dial 38 can be made only linearly proportional to reference pulse width but also directly reading in arbitrary units, for example milliseconds or seconds.

The reference pulse 123 is buffered by amplifier 49 and applied to input terminal 50 of circuit 40. Similarly, the unknown pulse is buffered by amplifier 45 and applied to input terminal 46 of circuit 40. Circuit 40, in turn, provides an indication of which of the two pulses have the longer width or time duration.

The initial condition of circuit 40, absent the presence of signals applied to terminals 46 and 50, is dependent on the previous input signal situation or on chance conditions caused by power turn on transients. Thus one transistor will be nonconducting with the other conducting. The initial condition is unimportant in that it will not in any way affect subsequent operation of the circuit. Assuming an input pulse width narrower than the reference pulse width the following sequence of events will occur. Both reference and input signals will be present at 46 and 50 as bias levels which will cause transistors 105 and 106 to be nonconducting. The input pulse then will disappear causing 46 to assume a voltage that makes transistor 105 conduct and leaving 106 in the non-conducting state. At the end of the reference pulse, transistor 106 will remain nonconducting because collector of transistor 105 is at zero level; the meter 41 will swing to the left (zero value) indicating that the input pulse is narrower than the reference pulse. This indication remains or is maintained until the next set of input and reference signals arrive at terminals 46 and 50, respectively. In the alternate condition, the reference pulse disappears first and the output of amplifier 49 goes to a bias level that cause transistor 106 to conduct, leaving transistor 105 nonconducting. When the input pulse disappears transistor 105 remains nonconducting because the collector of transistor 106 is at zero level. The meter 41 therefore will deflect to the right (full scale) indicating an input pulse that is wider than the reference pulse. This indication remains or is maintained until the next set of input and reference signals arrive at terminals 46 and 50, respectively.

The apparatus of the invention enables an operator to compare the time duration of an unknown electrical pulse to the time duration of a precise, calibrated, internally-generated pulse. In a situation where input pulses occur repetitively, the operator, by making successive comparison readings, can obtain the true value of the input pulse width with an accuracy essentially as good as the calibration of the reference pulse producing means. If the input pulse represents a single event, the apparatus will establish within very close tolerances whether the input pulse is longer or shorter than any arbitrary pulse width dialed into the apparatus by the operator. By involving the operator in this manner, the apparatus affords a highly accurate pulse width determination while at the same time utilizing simple, reliable and inexpensive circuitry. The fact that the comparison means holds or maintains the indication until the next set of input and reference pulses arrives, due to the nature of the bistable circuit therein, is particularly advantageous in situations where the operator must perform certain other tasks before he can visually inspect the indicator. The method of operation embodied in the present invention is particularly compatible with the fairly common class of function where an input pulse requires precise adjustment to a desired value.

The apparatus of the present invention has advantageous application in medical electronics for measuring the pulse width of signals occurring in the body of a patient, such as the external artifact caused by an implanted pacemaker and silent intervals in Electromyograms. The EMG silent period measurements constitute single events, in which it is important to know if a specific attribute of the EMG, i.e. the silent period, is longer or shorter than some normal value. The apparatus of the present invention in this instance is set at the normal value and an immediate indication is obtained as to the neurological state of certain muscles. Electrodes placed on the cheek of the patient are connected to the input of the apparatus, and the physician then taps the patient's jaw and observes from the meter whether the silent period is greater or less than the normal value. Pacemaker artifact pulses are repetitive, and the apparatus of the present invention can be used to determine the exact width of an unknown pulse and to reset the pacemaker pulse to a new desired value. The apparatus also can be used to indicate a change in pacemaker pulse width as an indication of decline in pacemaker battery voltage.

Figure 3:
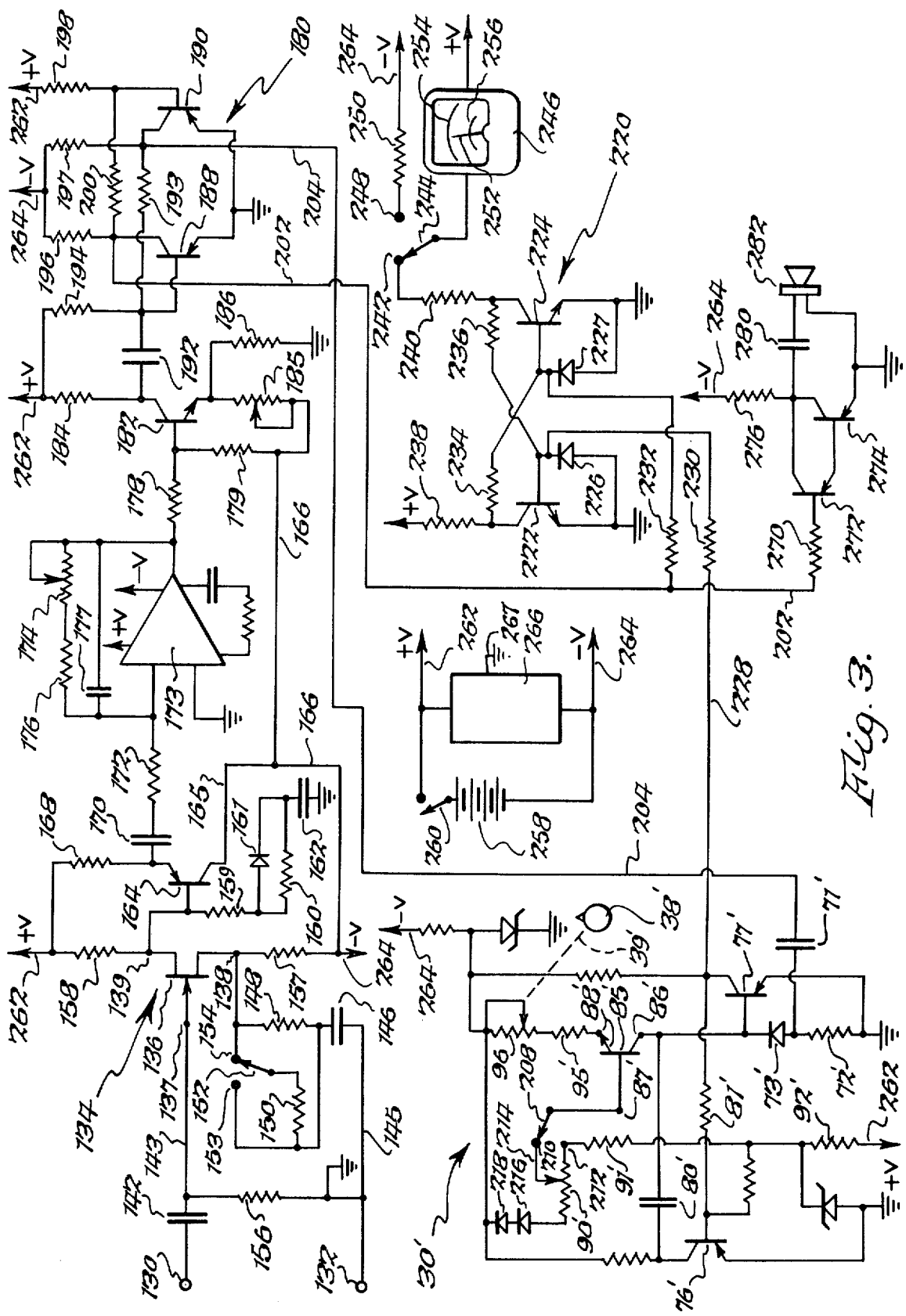
FIG. 3 is a schematic diagram of pulse width measuring apparatus according to the present invention for monitoring the artifact pulse signal occurring in the body of a patient from an implanted cardiac pacemaker.

Referring now to FIG. 3, apparatus for monitoring the operation of an implanted cardiac pacemaker includes a pair of sensing electrodes 130, 132 adapted to be operatively connected to the body of a patient. These electrodes can be of the class typically used for measuring biopotentials, such as EKG signals. For example, both electrodes can be of the expanding band type arm electrode. Electrodes 130, 132 are coupled to the input of a circuit 134 for limiting the dynamic range or amplitude of the incoming signal. In particular, circuit 134 includes an amplifier having a high input impedance and an adjustable gain in the form of a field effect transistor stage 136 having gate, source and drain terminals 137, 138 and 139, respectively. Electrode 130 is connected to one terminal of a coupling capacitor 142, the other terminal of which is connected by a lead 143 to gate terminal 137. Electrode 132 is connected to the electrical ground or reference of the circuit and through a lead 145 to one terminal of a capacitor 146, the other terminal of which is connected through a resistor 148 to source terminal 138 of transistor 136. The junction of capacitor 146 and resistor 148 is connected to one terminal of a resistor 150, the other terminal of which is connected to a switch arm 152 which is movable between switch contacts 153 and 154. Contact 153 is connected to the terminal of resistor 150 which is connected to the junction of capacitor 146 and resistor 148, and contact 154 is connected to the junction of resistor 148 and source terminal 138. Resistors 148 and 150 together with switch 152 comprise an adjustable gain control network for amplifier stage 136. When switch arm 152 engages contact 154 the parallel combination of resistors 148 and 150 is connected to source terminal 138 of transistor 136 with the result that the amplifier gain is relatively high. When switch 152 is in a position engaging contact 153, only resistor 148 is connected in circuit with source terminal 138 with the result that the amplifier gain is relatively lower. An input resistor 156 is connected across leads 143 and 145, and biasing resistors 157 and 158 are connected to the source and drain terminals 138 and 139, respectively, of field effect transistor 136. Resistor 157 is connected to a source of relatively negative bias voltage for the circuit, and resistor 158 is connected to a source of relatively positive bias voltage for the circuit. An automatic or signal responsive gain control circuit also is connected to amplifier stage 136. In particular, drain terminal 139 is connected to one terminal of a resistor 159, the other terminal of which is connected through the parallel combination of a resistor 160 and a germanium diode 161 to one terminal of a capacitor 162, the other terminal of which is connected to the electrical ground or reference point for the circuit.

Circuit 134 includes another stage in the form of a PNP transistor 164 which is connected as an emitter follower. In particular, the base terminal of transistor 164 is connected to drain terminal 139 of transistor 136, the collector terminal is connected by leads 165, 166 to the source of negative bias voltage for the circuit, and the emitter terminal of transistor 164 is connected through a resistor 168 to the source of positive bias voltage for the circuit.

The output of circuit 134 is differentiated by a capacitor 170, one terminal of which is connected to the emitter of transistor 164 and the other terminal of which is connected through a resistor 172 to one input of a differential amplifier 173. The other input of amplifier 173 is connected to the ground or electrical reference point for the circuit. A feedback network which determines the derivative gain of amplifier 173 comprises the series combination of a potentiometer 174 and a fixed resistor 176 connected between the output of amplifier 173 and the input terminal to which resistor 172 is connected. A capacitor 177 is connected in parallel with potentiometer 174 and resistor 176 to insure stable operation of amplifier 173. A pair of voltage dropping resistors 178, 179 are connected between the output of amplifier 173 and the negative bias voltage line 166.

The output of amplifier 173 is coupled to a circuit 180 for producing a standardized pulse having a width or time duration equal to the real or true width or time duration of the pacemaker pulse. In particular, the junction of resistors 178 and 179 is connected to the base terminal of an NPN transistor amplifier 182. The collector terminal of transistor 182 is connected through a biasing resistor 184 to the source of positive bias voltage for the circuit. The emitter terminal of transistor 182 is connected through a potentiometer or variable resistor 185 to negative bias voltage line 166 and through a fixed resistor 186 to the ground or reference of the circuit. The circuit 180 further comprises a pair of transistors 188 and 190 of the PNP type connected in a multivibrator configuration. The collector terminal of transistor 182 is connected to one terminal of a capacitor 192, the other terminal of which is connected to the base terminal of transistor 188 and through a resistor 193 to the collector terminal of transistor 190. The base terminal of transistor 188 also is connected through a resistor 194 to the source of positive bias voltage. The emitter terminals of transistors 188 and 190 both are connected to the circuit electrical ground or reference. The collector terminals of transistors 188 and 190 are connected through resistors 196 and 197, respectively, to the source of negative bias voltage. The base terminal of transistor 190 is connected through a resistor 198 to the source of positive bias voltage and through a resistor 200 to the collector terminal of transistor 188. Circuit 180 includes two output lines or leads 202 and 204 connected to the collector terminals of transistors 188 and 190, respectively.

One output of circuit 180 is connected by line 204 to the input of a reference pulse producing means 30' which is similar to pulse producing means 30 of the embodiment of FIGS. 1 and 2. For convenience in illustration, like components are indicated by similar numbers provided with a prime superscript. In accordance with this embodiment of the present invention, base terminal 87' of transistor 85' is connected to a switch arm 208 movable between contacts 210 and 212. Contact 210 is connected to the movable wiper arm 214 of potentiometer 90'. Contact 212 is connected to the junction of potentiometer 90' and fixed resistor 91'. A pair of diodes 216, 218 are connected between potentiometer 90' and the circuit negative voltage bias source to provide temperature compensation.

The circuit of FIG. 3 further comprises a comparison means 220 which determines whether the unknown pulse, in the present instance the pacemaker artifact, is longer or shorter than the internally generated pulse, provides a visual display of the determination, and stores the information to maintain the indication until the next artifact pulse arrives. Comparison means 220 is similar in operation to comparison means 40 of the circuit of FIGS. 1 and 2. In particular, circuit 220 includes first and second switching transistors 222 and 224, respectively, both of the NPN variety and connected together in a bistable multi-vibrator configuration. The emitter terminals of transistors 222 and 224 both are connected to the electrical reference or ground. In addition, protective diodes 226 and 227 are connected between the base terminals of transistors 222 and 224, respectively, and the reference or ground and are poled to protect the base terminals from negative voltages. The output of reference pulse producing means 30' is connected by a line 228 through a resistor 230 to the base terminal of transistor 222. Output line 202 from circuit 180 is connected to one terminal of a resistor 232, the other terminal of which is connected to the base terminal of transistor 224. The collector terminal of transistor 222 is connected through a resistor 234 to the base terminal of transistor 224 and, similarly, the collector terminal of transistor 224 is connected through a resistor 236 to the base terminal of transistor 222. The collector of transistor 222 also is connected through a biasing resistor 238 to the source of positive bias voltage. The collector terminal of transistor 224 is connected through a resistor 240 to a contact 242 engagable by a switch arm 244 which is connected to an indicator in the form of a meter 246 the other terminal of which meter is connected to the source of positive bias voltage for the circuit. A second switch contact 248 is connected through a resistor 250 to the source of negative bias voltage for the circuit. When switch arm 244 is in a position engaging contact 242, the relative width of the pacemaker artifact signal as compared to the internally generated pulse is determined by visually observing the position of pointer 252 relative to a first scale 254 of meter 246. When switch arm 244 is in a position engaging contact 248, the condition of the batteries included in the power supply for the circuit can be observed by reading the position of pointer 252 relative to a second scale 256 on meter 246.

The positive and negative bias voltages for the circuit of FIG. 3 are provided by a battery 258, the positive terminal of which is connected through a switch 260 to a line 262 which is connected to various points in the circuit as indicated by the +V notation at these points in the circuit. The negative terminal of battery 258 is connected by a line 264 to the various points in the circuit requiring a negative bias voltage as indicated by the −V notation at those points. A center voltage regulating network 266 can be connected across the combination of battery 258 and switch 260 to insure that a true center potential, i.e. a true battery center tap, is maintained even if one of the battery cells should fail. This in turn assures that the bias voltages on lines 262 and 264 remain equal and opposite. Network 266 can include a differential amplifier connected as a voltage follower wherein the voltages on lines 262, 264 are connected through appropriate resistance-capacitance networks to the inputs of the amplifier. The true center potential available on line 267 is provided at the amplifier output which is connected to lines 262, 264 through capacitance networks.

The output of circuit 180 on line 202 also is connected to the input of circuit means for providing an audible indication in response to each pacemaker artifact pulse. In particular, line 202 is connected through a resistor 270 to the base terminal of a transistor 272, the collector terminal of which is connected to the collector terminal of a second transistor 274. The base terminal of transistor 274 is connected to the emitter terminal of transistor 272. The emitter terminal of transistor 274 is connected to the electrical reference or ground. The collectors of transistors 272 and 274 are connected through a resistor 276 to the source of negative bias voltage. The collector terminal of transistor 274 also is connected to one terminal of a capacitor 280, the other terminal of which is connected to one input terminal of a conventional loudspeaker 282. The other terminal of speaker 282 is connected to the electrical reference or ground.

The circuit of FIG. 3 operates in the following manner. The nature and position of electrodes 130 and 132 and also the position of switch arm 152 depend upon the type of electrode scheme of the pacemaker implanted in the patient. If the pacemaker electrodes and leads are of the bipolar type, switch 152 is moved into engagement with contact 154. One practical electrode scheme found to perform satisfactorily would be as follows. Both electrodes 130, 132 were of the expanding band type positioned on the patient's right arm and on his left leg. Alternatively, one of the electrodes was an expanding band type placed on the patient's arm and the other electrode held by hand and placed on the body surface immediately over the implanted pacemaker. If the pacemaker electrode and leads are of the unipolar type, switch 152 is moved into engagement with contact 153 and in the practical embodiment both electrodes 130. 132 were of the expanding band arm type, although other electrode placements can be used.

To place the circuit in operation, switch arm 244 is moved into position engaging contact 242 and switch 260 is closed. Each pacemaker artifact signal or pulse is processed by circuit 134 in a manner limiting the amplitude of the dynamic range of the signal so that an accurate sampling or inspection of the width or time duration of the pulse signal can be made. In particular, field effect transistor 136 has a high input impedance, and the gain is set to be either relatively low or relatively high by having switch arm 152 engage either contact 153 or contact 154 depending whether the pacemaker electrode type is unipolar or bipolar. In addition, the combination of resistor 159, resistor 160, diode 161 and capacitor 162 connected between drain terminal 139 of transistor 136 and the electrode reference or ground serves as a signal or automatic gain control for the circuit. When the incoming signal is relatively small in amplitude, diode 161 does not conduct and the signal in effect sees the magnitude of resistor 160 which is considerably larger than that of resistor 150. On the other hand, when the incoming signal is relatively large, diode 161 is forward biased into conduction with the result that the signal in effect sees resistor 159 which is relatively small in magnitude. If the incoming signal is extremely large in amplitude, diode 161 will affect the loading on drain terminal 139 of transistor 136 so as to reduce the gain of the circuit. Capacitor 162 serves as a short for a.c. signals.

In pacemaker artifact pulse signals, the leading edge is larger or greater in amplitude than the trailing edge of the pulse and circuit 134 is constructed to have a smaller gain for the leading edge and to have preference or more gain for the trailing edge. Transistor 164 is connected in the circuit as an emitter follower to have a directional preference for the trailing edge, that is the full current capability of transistor 164 is applied to the trailing edge of the artifact signal.

According to a preferred mode of the present invention, transistor 136 is of the 2N3822 type with the casing being connected to the circuit reference or ground, resistor 159 has a magnitude of 150 ohms, resistor 160 has a magnitude of 1.2 megohms, diode 161 is of the 1N270 type, resistor 148 has a magnitude of 10 kilohms, resistor 150 a magnitude of about 540 ohms or less, capacitor 146 a magnitude of about 10 microfarads, and capacitor 162 has a magnitude of about 50 microfarads. Resistors 157 and 158 have magnitudes of 22 kilohms and 10 kilohms, respectively.

Circuit stage 134 thus performs an amplitude compression on the pacemaker artifact signal and transforms a relatively high impedance at the input of the stage to a relatively low impedance at the output thereof. In other words this stage conditions the artifact pulse by limiting the dynamic range or amplitude thereof. The next stages of the circuit of FIG. 3 serve to provide a standardized pulse having a width or time duration which accurately represents the width or time duration of pacemaker pulse giving rise to the artifact signal. In particular, the signal is differentiated by capacitor 170 whereby both the beginning of the rise and the beginning of the fall of the signal are detected. A true or accurate representation of the width of the artifact pulse results from this sampling. This produces a positive-going and negative-going spikes or pulses corresponding to the leading edge and trailing edge, respectively, of the artifact signal, and these spikes or pulses are amplified by amplier 173. Amplifier 173 thus produces an output pulse at a time corresponding to when the artifact signal begins its rise and produces another output signal at a time when the artifact signal begins its fall. Variable resistor 174 and fixed resistor 176 in the feedback loop of amplifier 173 determined the derivative gain, and the capacitor 177 is provided to prevent ringing and assure stable operation of the amplifier. The output signals from amplifier 173 are applied to a transistor amplifier 182 having an adjustable gain determined by the setting of potentiometer 185. Amplifier 182 provides a positive driving signal or current spike and a negative driving signal or current spike corresponding to the beginning of rise and beginning of fall, respectively, of the artifact signal. These signals are applied as trigger pulses to the circuit including transistors 188 and 190 connected in a set-reset flip-flop configuration.

On each of the lines 202 and 204 connected to the collectors of transistors 188 and 190, respectively, there appears a fixed square pulse which starts or rises at a time corresponding to when the pacemaker artifact pulse rises and which ends or falls at a time corresponding to the time when the pacemaker artifact signal falls. In particular, the quiescent or initial condition of circuit is with transistor 188 on or conducting and transistor 190 off or non-conducting. As a result, line 202 is at the ground or reference voltage level and line 204 is at a relatively negative voltage level. In response to a positive-going trigger pulse corresponding to the rise or the leading edge of the artifact signal, transistor 188 is turned off and transistor 190 is turned on. This, in turn, switches the voltage on line 202 to a relatively negative value and switches the voltage on line 204 to the ground or reference level. Then after a time corresponding to the time duration or width of the artifact signal, a negative-going trigger signal appears which switches transistor 188 on and transistor 190 off. As a result, the voltage on line 202 is switched back to the ground or reference level and the voltage on line 204 is switched back to the relatively negative voltage level. In summary, for each pacemaker artifact signal a negative-going square pulse is present on line 202 and a positive-going square pulse, i.e. from a relatively negative to the ground level, is present on line 204 for each artifact signal.

The positive-going square pulse on line 204 is applied to the input of the reference pulse producing means 30' which generates an output reference pulse on line 228 in a manner substantially similar to that of reference pulse producing means 30 of FIG. 1. The operation of the portion including switch 208 will be described in detail presently. The negative-going pulse on line 202 is applied simultaneously through resistor 232 to the base of transistor 224 in comparison means 220 and through resistor 270 to the base of transistor 272 of the audio indicator circuit. For each pulse present on line 202 corresponding to a pacemaker artifact signal, this pulse is amplified by transistor 272 to turn on transistor switch 274 allowing capacitor 280 to discharge through speaker 282 thereby providing an audible sound, in particular an audio click. The provision of a transistor switching circuit for discharging a capacitor through the speaker insures that a signal of sufficient amplitude is provided to give an audible indication. An audible click will be heard if sensing electrodes 130, 132 are properly connected to the patient and if the pacemaker is functioning. In most cases a comparison between click rate and pulse rate can be used to verify capture.

Comparison means 220 operates in a manner similar to that of comparison means 40 in the embodiment of FIGS. 1 and 2. Thus both the input and reference pulses present on lines 202 and 228, respectively, will cause both transistors 222 and 224 to be nonconducting. If the input pulse is of shorter width or time duration than the reference pulse, the input pulse will disappear first causing transistor 224 to conduct and leaving transistor 222 in the non-conducting state. At the end of the reference pulse, transistor 222 will remain non-conducting because the collector of transistor 224 is at zero level. The pointer 252 of meter 246 will swing in one direction from a designated part such as the center of scale 254 to indicate that the input pulse, i.e. the pulse representing the pacemaker artifact signal, is narrower than the reference pulse. The flip-flop circuit of transistors 222 and 224 causes this indication provided by meter 246 to remain or be maintained until the next set of input and reference signals arrive. In the alternate condition where the input pulse is of longer width or time duration than the reference pulse, it will be seen by proceeding through a similar analysis that the pointer 252 of meter 246 will swing in the opposite direction away from the center of scale 254. This indication remains or is maintained until the next set of input and reference signal arrives.

The circuit of FIG. 3 provides a self sufficient and portable instrument which is a convenient and accurate means of validating the performance of an implanted pacemaker. In other words it allows a patient to self check his pacemaker anytime he desires. The instrument provides a simple yes or no indication whether the pacemaker pulse width has deviated by a preset percentage from its initial value. Changes in the pacemaker pulse width are the prime indicators of battery depletion or loss of battery cells. In particular, the instrument control parameter, i.e. pulse width, is adjusted to the specific, initial or beginning of life parameter of the implanted pacemaker. The instrument then will indicate when the pulse generator output, i.e. the pacemaker pulse which gives rise to the artifact pulse, has deviated from that initial value by a set percentage.

Referring now to reference pulse producing means 30' in the circuit of FIG. 2, with the circuit properly connected to the patient as described above, switch arm 208 is moved into engagement with contact 212 and knob 38' is rotated slowly until pointer 252 just switches between designated regions of the meter scale, for example the regions to the left and the right of the center or mid-point of scale 254. As a result, the width of the reference pulse is made equal to the width of the pacemaker artifact pulse. Then switch arm 208 is moved into engagement with contact 210 and pointer 252 will move to the region on one side of the midpoint of scale 254. For convenience this region can be colored green on the meter dial face to indicate a region of safety, and the region to the opposite side of the center of scale 254 can be colored red to indicate the point at which the pacemaker should be checked. Switching potentiometer 90' into the circuit of base terminal 87' of transistor 85, decreases the positive bias voltage thereon decreasing the collector current and hence increasing the width of the reference pulse on line 228. The percentage increase in the width of the reference pulse is predetermined by the setting of potentiometer 90', and according to a preferred mode of the present invention this percentage is ten percent.

With the instrument conditioned or preset by the physician as described, it can be disconnected from the patient and turned off for storage, and then periodic tests can be made subsequently by the physician or patient simply by reconnecting the electrodes 130, 132 to the patient and turning the instrument on. Pointer 252 will remain in the green area indicating safe or normal pacemaker operation until the width of the pacemaker artifact pulse increases by 10%. Then pointer 252 will move to the red area indicating that the pacemaker should be checked. In other words, the instrument will indicate a percentage deviation from the control value, which is the original value of that specified implanted pacemaker.

The setting of potentiometer 90' to indicate a 10% change in pacemaker pulse width is based on clinical specification and can of course be varied to meet different specifications. According to a preferred mode of the present invention, potentiometer 90' is rated at 22K and resistors 91' and 92' have magnitudes of 39K and 6.8K, respectively. The circuit of FIG. 3 is constructed to signal an increase in pacemaker artifact pulse width which for many pacemakers current in use is an indication of decline in battery voltage. For those pacemakers wherein decline in battery voltage is indicated by a decrease in pacemaker pulse width, the circuit of FIG. 3 is readily adaptable. This is accomplished by simply interchanging terminals 210 and 212 of switch 208, connecting meter 246 and its circuit including switch arm 244 and contact 242 to the collector circuit of transistor 222 through resistor 238, and connecting the collector circuit of transistor 224 to the +V supply through resistor 240.

It is therefore apparent that the present invention accomplishes its intended objects. While two embodiments of the present invention have been described in detail, this is for the purpose of illustration, not limitation.

We claim:
1. Electrical pulse width measuring aparatus comprising:
   a. comparison means having first and second inputs and responsive to input pulse time duration for providing an indication of relative pulse width, said comparison means including means for maintaining said indication until another pulse arrives;
   b. means for applying an input pulse of unknown time duration to one input of said comparison means;
   c. means for producing a reference pulse of known time duration, said reference pulse producing means being coupled through circuit means to adjustable means whereby the time duration of the reference pulse is linearly proportional to the position of said adjustable means;

d. means for applying the output of said reference pulse producing means to the other input of said comparison means; and
  e. synchronizing means coupled to said reference pulse producing means and said means applying unknown pulses for synchronizing the production of a reference pulse with the presence of an unknown pulse;
  f. whereby said comparison means provides an indication of whether the time duration of the unknown pulse is less than or greater than the duration of the reference pulse.

2. Apparatus according to claim 1, wherein said means for applying an input pulse comprises amplifier means having threshold adjusting means for controlling the region on the input pulse at which duration is measured.

3. Apparatus according to claim 1, wherein said comparison means comprises a two state flip-flop circuit, the final state of which is determined by the input pulse of longer time duration.

4. Apparatus according to claim 1, wherein said synchronizing means comprises means for producing a trigger pulse from the leading edge of said unknown pulse.

5. Electrical pulse width measuring apparatus comprising:
  a. comparison means having first and second inputs and responsive to input pulse time duration for providing an indication of relative pulse width, said comparison means including means for maintaining said indication until another pulse arrives, said comparison means comprising a two state flip-flop circuit, the final state of which is determined by the input pulse of longer time duration;
  b. means for applying an input pulse of unknown time duration to one input of said comparison means;
  c. means for producing a reference pulse of known time duration, said reference pulse producing means being coupled through circuit means to adjustable means whereby the time duration of the reference pulse is linearly proportional to the position of said adjustable means;
  d. means for applying the output of said reference pulse producing means to the other input of said comparison means;
  e. synchronizing means coupled to said reference pulse producing means and said means applying unknown pulses for synchronizing the production of a reference pulse with the presence of an unknown pulse;
  f. said flip-flop circuit of said comparison means comprising a pair of switching transistors connected together in a bistable multivibrator configuration, means for connecting the unknown and reference pulses to corresponding base terminals of said transistors and meter means responsive to an electrical quantity connected in the output circuit of one of said transistors whereby said comparison means provides an indication of whether the time duration of the unknown pulse is less than or greater than the duration of the reference pulse.

6. Electrical pulse width measuring apparatus comprising:
  a. comparison means having first and second inputs and responsive to input pulse time duration for providing an indication of relative pulse width, said comparison means including means for maintaining said indication until another pulse arrives;
  b. means for applying an input pulse of unknown time duration to one input of said comparison means;
  c. means for producing a reference pulse of known time duration, said reference pulse producing means including energy storage means whereby the time duration of the reference pulse is proportional to the current flowing through said energy storage means, said reference pulse producing means being coupled through circuit means to adjustable means whereby the time duration of the reference pulse is linearly proportional to the position of said adjustable means, said circuit means including a current source connected in controlled relation to said adjustable means and in controlling relation to said energy storage means whereby the magnitude of current flowing through said energy storage means is linearly proportional to the position of said adjustable means, said adjustable means being manually operable;
  d. means for applying the output of said reference pulse producing means to the other input of said comparison means; and
  e. synchronizing means coupled to said reference pulse producing means and said means applying unknown pulses for synchronizing the production of a reference pulse with the presence of an unknown pulse;
  f. whereby said comparison means provides an indication of whether the time duration of the unknown pulse is less than or greater than the duration of the reference pulse.

7. Electrical pulse width measuring apparatus comprising:
  a. comparison means having first and second inputs and responsive to input pulse time duration for providing an indication of relative pulse width, said comparison means inclunig means for maintaining said indication until another pulse arrives;
  b. means for applying an input pulse of unknown time duration to one input of said comparison means;
  c. means for producing a reference pulse of known time duration, said reference pulse producing means comprising a monostable multivibrator having a timing capacitor, said reference pulse producing means being coupled through circuit means to adjustable means whereby the time duration of the reference pulse is linearly proportional to the position of said adjustable means, said circuit means including a transistor, the collector emitter circuit of which is connected between a source of voltage and said timing capacitor, and said adjustable means comprising a variable resistance connected in the emitter circuit of said transistor, whereby for any given voltage applied to the base of said transistor, the current charging said capacitor is linearly proportional to the setting of said variable resistance;
  d. means for applying the output of said reference pulse producing means to the other input of said comparison means; and
  e. synchronizing means coupled to said reference pulse producing means and said means applying unknown pulses for synchronizing and the production of a reference pulse with the presence of an unknown pulse;
  f. whereby said comparison means provides an indication of whether the time duration of the unknown pulse is less than or greater than the duration of the reference pulse.

* * * * *